United States Patent
Jawale et al.

(10) Patent No.: US 11,771,634 B2
(45) Date of Patent: Oct. 3, 2023

(54) ANTIMICROBIAL ANTIFUNGAL COMPOSITION

(71) Applicant: GODREJ INDUSTRIES LIMITED, Mumbai (IN)

(72) Inventors: Arun Harachandra Jawale, Mumbai (IN); Sandeep Dattatray Gharat, Mumbai (IN); Akash Bharat Gaikwad, Mumbai (IN)

(73) Assignee: GODREJ INDUSTRIES LIMITED, Mumbai (IN)

(*) Notice: Subject to any disclaimer, the term of this patent is extended or adjusted under 35 U.S.C. 154(b) by 0 days.

(21) Appl. No.: 17/648,018

(22) Filed: Jan. 14, 2022

(65) Prior Publication Data

US 2022/0233422 A1    Jul. 28, 2022

(30) Foreign Application Priority Data

Jan. 16, 2021    (IN) .............................. 202121002118

(51) Int. Cl.
| | |
|---|---|
| A61K 8/55 | (2006.01) |
| A61Q 5/00 | (2006.01) |
| A61K 8/73 | (2006.01) |
| A61Q 5/02 | (2006.01) |

(52) U.S. Cl.
CPC ............... *A61K 8/556* (2013.01); *A61K 8/73* (2013.01); *A61Q 5/006* (2013.01); *A61Q 5/02* (2013.01); *A61K 2800/436* (2013.01); *A61K 2800/5426* (2013.01); *A61K 2800/596* (2013.01); *A61K 2800/74* (2013.01)

(58) Field of Classification Search
None
See application file for complete search history.

(56) References Cited

U.S. PATENT DOCUMENTS

| | | | |
|---|---|---|---|
| 3,385,755 | A | 5/1968 | Seebohm et al. |
| 4,307,089 | A | 12/1981 | Melloh et al. |
| 5,286,719 | A | 2/1994 | Fost et al. |
| 5,648,348 | A | 7/1997 | Fost et al. |
| 6,333,027 | B1 | 12/2001 | Hopkins et al. |
| 6,410,593 | B1 | 6/2002 | De Mesanstourne et al. |
| 7,518,005 | B2 | 4/2009 | Patil et al. |
| 2004/0242501 | A1 | 12/2004 | Gross et al. |
| 2009/0298956 | A1* | 12/2009 | Chowhan ............. A61K 9/0046 514/785 |

FOREIGN PATENT DOCUMENTS

| | | |
|---|---|---|
| CN | 104095766 A | 10/2014 |
| WO | 2006069175 | 6/2006 |

OTHER PUBLICATIONS

Yoo et al.; "Characteristics of Microbial Biosurfactant as an Antifungal Agent Against Plant Pathogenic Fungus"; J. Microbial Bltechmol. (2005), 15(6), p. 1164-1169.

Myriam Rincon-Fontan et al.; "Novel Mulitfunctional Biosurfactant Obtained from Corn as a Stabilizing Agent for Antidandruff Formulations . . . "; AC Omega 2020, 5, 5704-5712.

* cited by examiner

*Primary Examiner* — Brian Gulledge
(74) *Attorney, Agent, or Firm* — Kramer & Amado, P.C.

(57) ABSTRACT

A synergistic antimicrobial composition for use in personal care products functions as an antifungal agent in hair shampoo and hair care products, and includes (A) an undecylenic acid based phosphobetaine depicted by Formula I, where R=Undecylenic acid:

Formula I

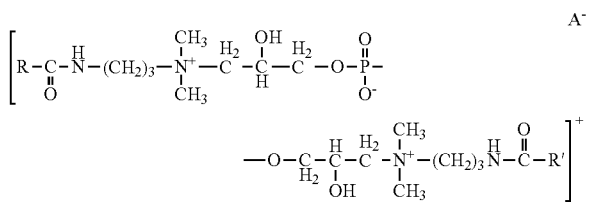

and (B) a sophorolipid, a biosurfactant produced by a fermentation process using *Candida bombicola*, having a structure as depicted by Formula II(A), Formula II(B), or a mixture thereof:

Formula II(A)

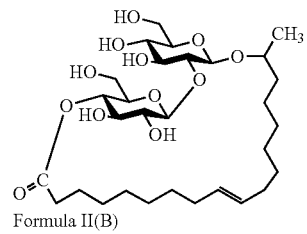

Formula II(B)

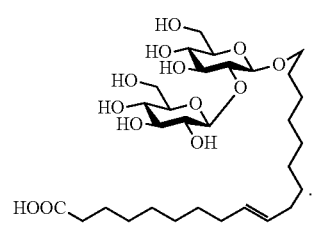

20 Claims, 1 Drawing Sheet
(1 of 1 Drawing Sheet(s) Filed in Color)

ANTIMICROBIAL ANTIFUNGAL COMPOSITION

FIELD OF INVENTION

The present invention relates to water soluble, highly substantive, scalp & skin compatible yet effective antimicrobial compounds and compositions thereof. More particularly the present invention relates to synthetic phospholipids which can be used as an antifungal agent in personal care products particularly in hair care products and the compositions thereof.

BACKGROUND OF THE INVENTION

Dandruff is a problem for many people around the world. Dandruff is white in colour and has an aesthetically unpleasant appearance. It is widely believed that *Malassezia* yeasts, such as *Malassezia furfur*, are the main cause of dandruff. One of the main intervention strategies, conventionally used in the market for the treatment of dandruff is the topical application of antifungals. These antifungal agents remove or reduce the level of the *Malassezia* and provide effective treatment of the dandruff.

An ideal antidandruff agent must not only relieve the flaking and itching symptoms of dandruff, but also must be substantive to the skin and hair in order to extend the efficacy of the antidandruff agent from one shampoo treatment to the next.

Further, it is desirable that anti-dandruff actives demonstrate greater than 99.9% killing of the dandruff causing bacteria (*M. furfur*) that corresponds to minimum log 3 reduction within five-minute residence time through antidandruff shampoo and other hair preparation.

Furthermore, it is also desirable that anti-dandruff actives are deposited in a way that does not significantly impact their bioavailability on the scalp surface; it means antidandruff actives must be substantive to the scalp and hair in order to extend the efficacy of the antidandruff active from one shampoo treatment to the next.

Moreover, it is desired that the antidandruff actives and preparations thereof, must be stable and effective at natural pH of the scalp or skin (i.e., pH 4.0-5.0) required maintain healthy scalp & skin. Additionally, it is also desired that the anti-dandruff actives are compatible with cosmetic ingredients and easy to formulate and provide colour and heat stable formulation.

the products currently available in the markets are particulate antidandruff agents which are insoluble in aqueous media or water insoluble, and are normally delivered in form of a shampoo.

The water-insoluble particulate antidandruff agent tends to separate out from the aqueous hair shampoo base, due to difference in the density of anti-dandruff ingredient and the continuous phase of the composition. The aforementioned density mismatch leads to compositional instability. In systems containing anti-dandruff materials with a density less than that of the continuous phase, the anti-dandruff material tends to float to the top surface of the continuous phase (i.e., creaming). In systems containing insoluble materials with a density greater than that of the continuous phase, the insoluble materials tend to sink to the bottom of the continuous phase (i.e., settling).

Suspended insoluble antidandruff particles have a tendency to aggregate in aqueous cosmetic products thus decreasing its available surface area with a consequential loss of antidandruff activity. Thus, failure to adequately suspend the antidandruff agent leads to eventual shampoo separation as the antidandruff agent settles to the bottom of the container, and results in poor dandruff control and consumer complaints.

Many anti-dandruff actives are known to be used for this purpose, among which mention may be made of zinc pyrithione (ZnPTO), climbazole, octopirox, ketoconazole, coal tars, piroctone olamine, selenium disulfide and, more recently, tropolone and hinokitiol (Research Disclosure No. 429, January 2000).

The antidandruff activity of these substances towards *Malassezia* yeasts is not satisfactory, as in many cases, the reduction of dandruff is only moderate despite their regular use that too at higher concentrations. Furthermore, the action of these active agents does not show specificity, in the sense that it is not directed only towards the microorganism(s) directly responsible for the development of dandruff.

Further, some antidandruff actives among those most commonly used show cytotoxic potential in vitro. It is necessary to lower the working amounts thereof to below an acceptable cytotoxicity threshold, or even to combine them with molecules which protect the integrity of skin cells which are damaged or inflamed to a greater or lesser extent.

Furthermore, these products have other drawbacks: for example, piroctone-olamine poses coloration problems in shampoos containing this active principle, Zinc pyrithione being water insoluble powder requires suspending agent or structurant to make the stable formulation, which leads to opaque formulations that are unstable in light, climbazole is water-insoluble and requires the mandatory use of solvents (ethanol, benzyl alcohol).

Undecylenic acid, which is also commercially available, is used as an anti-dandruff agent in shampoos however it is a primary irritant and toxic substance. Therefore, it is not desired to have free undecylenic acid in the product.

U.S. Pat. No. 3,385,755 discloses antibacterial and antifungal agents derived from Undecylenic acid alkylolamide and its derivative like undecylenic acid monoalkylolamide sulfosuccinate half ester. However, no data on antidandruff activity of the molecule is provided to prove the efficacy of the antidandruff claim. Further, the US '755 does not discuss use of sophorolipid as an adjunct to the undecylenic acid derivative.

U.S. Pat. No. 4,307,089 discloses a cosmetic formulation consisting of pyrithione compound in combination with undecylenic acid monoalkylolamide sulfosuccinate half ester for treatment of dandruff. However, the issue related to stability of formulation with pyrithione remains unresolved.

U.S. Pat. No. 6,333,027 discloses a composition non-stinging to eyes to treat dandruff in which Undecylenamidopropyl betaine is one of the active ingredients.

U.S. Pat. No. 6,410,593 discloses the use of water soluble Undecylenamidopropyl betaine which offers the advantage of being able to constitute an amphoteric component of a shampoo which itself has the desired antidandruff properties.

U.S. Pat. No. 7,518,005 B2, and its corresponding Indian Patent Ns IN247743, discloses water-soluble Undecylenamidopropyl dimethyl hydroxyl ethoxy ethyl ammonium undecylenate compounds having more superior anti-dandruff activity because of the presence of two undecylenic acid moieties in the molecule.

The antidandruff compounds claimed by U.S. Pat. No. 7,518,005 B2 being a salt of undecylenic acid, it is necessary to maintain alkaline pH, as at lower pH, particularly at natural pH of the scalp (i.e., pH 4.0-5.0), it dissociates into quaternary ammonium salt and free undecylenic acid. As pointed out earlier, it is undesirable to have free undecylenic acid in the product, because it is an irritant and toxic substance. Therefore, the antidandruff active compounds of U.S. Pat. No. '005 B2 are not compatible with scalp and not suitable for use in antidandruff shampoo at pH of the scalp. Further, the invention claims the antidandruff compounds to be substantive, however no data on substantivity is provided.

U.S. Pat. Nos. 5,286,719 and 5,648,348 discloses a virucidal and antimicrobial compositions based on antidandruff phospholipids which show broad spectrum antimicrobial and virucidal activity suitable for use as preservative and/or disinfectant agent. The claims and efficacy data provided support antimicrobial and virucidal activity. It does not, however, disclose undecylenic acid-based phospholipids and its application as an anti-fungal agent, particularly as anti-dandruff active. However, there is no specific suggestion for undecylenic acid-based phospholipids and its use for anti-dandruff activity.

Sophorolipids (SLs) have been known for over 40 years, but because of growing environmental awareness, they recently regained attention as biosurfactants due to their biodegradability, low ecotoxicity, and production based on renewable resources. They have been found to be useful as stabilizing agent, surfactants, and antimicrobials active against fungal plant pathogens, spermicidal and virucidal in variety of formulations. SLs produced from *Candida bombicola* are reported to have antimicrobial activity. However, there is no prior art that describes SLs and also its combination with synthetic phospholipids application as an antifungal, particularly as anti-dandruff active.

PCT/US2005/046426 (WO2006/069175) describes sophorolipids and is used as the commercial antifungal agent. US 2004/0242501 discloses spermicidal and virucidal properties of sophorolipids. Yoo et al. (2005) and other researchers have reported that sophorolipids natural mixture (nonchemically modified) to be active against fungal plant pathogens.

CN104095766A discloses the synergy between ZnPTO and sophorolipids for anti-dandruff treatment.

ACS Omega 2020, 5, 5704-5712, Myriam Rincán-Fontan et al. describes use of corn based sophorolipids as multifunctional biosurfactant and stabilizing agent for antidandruff formulations based on ZnPTO powder.

All the above-mentioned antidandruff agents and compositions thereof have one drawback or the other and does not have the attributes necessary for the superior antidandruff activity.

Furthermore, none of the prior arts, disclose the antidandruff efficacy data, such as greater than 99.9% killing (>log 3 reduction) of dandruff causing bacteria viz: *M. furfur* within specific (normally five-minute) residence time, substantivity of antidandruff agent as a proof of substantiation through final antidandruff preparations, since the ingredients of the final preparations may have a negative effect on efficacy of the active.

Therefore, it would be advantageous to develop antidandruff compounds that are friendly to the microbial balance of the scalp, highly substantive for prolonged association with the hair and scalp and capable of destroying greater than 99.9% (or log 3 reduction) of the microorganisms responsible for dandruff at natural pH of the scalp (pH 4.0-5.0).

Hence, there exist a need for antidandruff compounds which have low degree of irritation, higher substantivity to hair & scalp, excellent compatibility with scalp (antidandruff active must work effectively at scalp pH 4.0-5.0 to maintain healthy scalp & skin), more effective antidandruff activity and easy to formulate in hair care preparations.

OBJECT OF INVENTION

Thus, it is the main object of the invention to provide a highly substantive water-soluble antidandruff compounds that overcome the problems associated with the prior art.

The further object of the present invention is to provide water soluble and highly substantive novel anti-fungal/anti-dandruff phospholipids.

The yet further object of the present invention is to provide water soluble and highly substantive anti-dandruff compounds that shows high antidandruff activity (>99.9% h killing or >log 3 reduction of dandruff causing bacteria).

One more object of the present invention is to provide water soluble and highly substantive anti-dandruff compounds that are derived from natural origin and easy to formulate in hair care preparations.

Another object of the present invention is to provide water soluble and highly substantive anti-dandruff compounds that are capable of providing scalp and skin friendly antidandruff shampoos, hair gels, conditioners and hair care products.

Yet another object of the present invention is to provide water soluble and highly substantive anti-dandruff compounds that are effective in wide pH range.

Still another object of the present invention is to provide water soluble and highly substantive anti-dandruff compounds that offer dual characteristics, as an amphoteric and a cationic component of a shampoo which provides the desired antimicrobial properties and compatibility with other ingredients of the shampoo.

The second object of the present invention is to provide hair care compositions containing the water soluble and highly substantive anti-dandruff compounds.

The third object of the present invention is to provide a method of treating the dandruff infected scalp with the hair care preparations having the water soluble and highly substantive anti-dandruff compounds.

SUMMARY OF INVENTION

In view of above objects, in first aspect the present invention provides naturally derived water soluble, substantive and highly effective novel anti-fungal/anti-dandruff phospholipids of the formula I.

Formula I

In the second aspect the invention provides naturally derived, water soluble, substantive and highly effective synergistic combinations of phospholipids of formula I with sophorolipids of formula II.

Formula II

R₃: H, CH₃
R₄: (CH₂)₁₅
(A)-a: R₁ = R₂ = COCH₃
(A)-b: R₁ = COCH₃, R₂ = H
(A)-c: R₁ = H, R₂ = COCH₃
(A)-d: R₁ = R₂ = H
(B)-a: R₁ = R₂ = COCH₃
(B)-b: R₁ = COCH₃, R₂ = H
(B)-c: R₁ = H, R₂ = COCH₃
(B)-d: R₁ = R₂ = H

In third aspect, the invention provides a personal care composition comprising compounds of Formula I and/or its synergistic combinations with formula II.

The fourth aspect of the invention is to provided method of treating the dandruff infection with the personal care compositions containing compounds of Formula I and/or its synergistic combinations with formula II comprising of topical application of an effective amount of the personal care composition

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Described herein is a novel, highly effective, cosmetically accepted anti-dandruff compounds and composition thereof.

The present inventors have surprisingly found that phospholipids having two undecylenic acid moieties bonded by organic covalent bonds, when used alone or in combinations with sophorolipids; not only have more superior antidandruff activity due to its high substantivity but also have the capability of producing antidandruff preparations at natural scalp pH and have compatibility with cosmetic ingredients, compared to prior art antidandruff actives.

The present inventors have also found that the compounds of the present invention provide attributes like antimicrobial preservative, conditioning and viscosity boosting properties to care compositions in addition to superior anti-dandruff properties.

The novel synthetic phospholipids of the present invention can be prepared by reaction between tertiary amine based on undecyl (C11) carbon chain of Formula III:

Formula III or tertiary amine based on undecylenamide of Formula IV:

Formula IV and phosphate esters of Formula V

Formula V

Such phospholipids can be prepared by reacting corresponding tertiary amine and phosphate ester reactants in the molar ratio of 1:1 to 3:1; preferably 2.0:1 to 2.5:1, of amine to phosphate ester. U.S. Pat. No. 4,283,542 can be referred for the detail process for the preparation of compounds of the present invention. These compounds are called as phosphobetaines or referred as "synthetic phospholipids" in the patent.

Phosphobetaine derivatives having, in general, quaternized alkyl amine groups and at least one phosphorous-containing anion in the molecule referred to hereinafter as "synthetic phospholipids" have been disclosed. These synthetic phospholipids are suggested as exhibiting an Phosphobetaines based on hydrophobes C8 to C18, saturated, mono/di/tri unsaturated fatty acids derived from vegetable oils such as coconut oil, sunflower oil, safflower oil, palm oil, castor oil, etc. are well known and established as a useful cosmetic ingredient. These synthetic phospholipids are known to exhibit antimicrobial activity and antiviral activity as well. However, undecylenic acid based phosphobetaines have still not be reported in prior art.

The components of the blends are naturally derived and are thus safe and biodegradable.

In an embodiment, the present invention covers a blend of an undecylenic acid based phosphobetaine (Formula I), sophorolipid based on vegetable oils (Formula II) shows synergistic effect in terms of antimicrobial and antifungal effect even at lower concentration in comparison with the individual ingredients.

(Formula I, where R = Undecylenic Acid)

(Formula II)

In particular, the current invention relates to use of synergistic blend for prevention of fungus, specifically dandruff. The synergistic blend of invention offers broad spectrum antimicrobial activity and more particularly effective against microorganisms causing skin disorders such as skin odor, dandruff, athlete's foot.

Accordingly, the blend consists of Undecylenic acid based phosphobetaine (Formula I) and sophorolipid (Formula II).

Undecylenic acid based phosphobetaine (Formula I) is a water-based surfactant with solid content of about 50%. Phosphobetaine derivatives having, in general, quaternized alkyl amine groups and at least one phosphorous-containing anion in the molecule referred to hereinafter as "synthetic phospholipids", have been disclosed. These synthetic phospholipids exhibit an outstanding combination of surfactant characteristics as well as being well tolerated by human tissue, i.e., they exhibit exceptionally low ocular irritation and oral toxicity.

In one more embodiment, the present invention provides various compositions containing compounds of the present invention in a suitable concentration. In accordance with this embodiment, the compositions can be surfactant based transparent solutions or opaque (pearly) preparations such as shampoos or emulsions such as conditioner, foot care cream, scalp sebum, hair tonic or/and hair gel etc.

In an embodiment, the novel synthetic phospholipids of the present invention can be prepared by reaction between tertiary amine based on undecyl (C11) carbon chain of Formula III Formula III or tertiary amine based on undecylenamide of Formula IV

Formula IV and phosphate esters of Formula V

Formula V

Such phospholipids can be prepared by reacting corresponding tertiary amine and phosphate ester reactants in the molar ratio of 1:1 to 3:1; preferably 2.0:1 to 2.5:1, of amine to phosphate ester. U.S. Pat. No. 4,283,542 can be referred for the detail process for the preparation of compounds of the present invention. These compounds are called as phosphobetaines or referred as "synthetic phospholipids" in the patent.

The sophorolipid of the formula II is produced by *C. bombicola*, which shows antimicrobial activity. Sophorolipids are surface-active compounds synthesized by a selected number of yeast species. They have been known for over 40 years, but because of growing environmental awareness, they recently regained attention as biosurfactants due to their biodegradability, low ecotoxicity, and production based on renewable resources.

The Sophorolipids shown by the two structures in Formula I, Sophorolipids (SLs) are glycolipid biosurfactant molecules produced by yeasts, such as *Candida bombicola, Yarrowi alipolytica, Candida apicola*, and *Candida bogoriensis*. Microbial bio-surfactants generally have an amphiphilic structure, possessing a hydrophilic moiety, such as an amino acid, peptide, sugar or oligosaccharide, and a hydrophobic moiety including saturated or unsaturated lipid or fatty acids. They lower surface and interfacial tension and form spherical micelles at and above their critical micelle concentration (CMC).

In the present invention, a natural mixture of sophorolipids is synthesized by fermentation of *Candida bombicola*. It consists of a hydrophilic carbohydrate head, sophorose, and a hydrophobic fatty acid tail with generally 16 or 18 carbon atoms with saturation or unsaturation. Sophorose is an unusual disaccharide that consists of two glucose molecules linked β-1, 2. The fatty carboxylic acid group is either free (acidic or open form) or internally esterified generally at the 4"-position (lactonic form). Thus, SLs of the present invention is a mixture of macro-lactones and free acid structures that are acetylated to various extents at the primary hydroxyl sophorose ring positions.

The antidandruff composition of the present invention is produced by just cold mixing phosphobetaine of formula I and sophorolipids of formula II in different proportions in the w/w ratio 1:9 to 9:1.

In an advantageous embodiment, the product of the invention demonstrates following advantages:
  Naturally derived, yet cost effective active
  Highly water soluble—easy incorporation
  No use of structurant or suspending agent required
  Provide color and heat stable antidandruff formulation
  Non-irritant to skin/scalp
  Transparent/Clear antidandruff formulations like shampoo, hair tonics
  Excellent performance at natural pH of scalp or skin (pH 4.0-5.0) required to maintain healthy scalp & skin
  Substantive to skin—leads to deposition on scalp for prolonged effect on the scalp
  Compatible with all surfactant types and cosmetic ingredients
  Stable over wide range of pH, temperature
  Excellent antidandruff efficacy
  Surfactant—Contributes to detergency, foaming and viscosity of the formulation
  Pearliness of the formulation is maintained In one of the embodiments the personal care cleansing compositions of the present invention comprises from 0.5 to 4% anti-dandruff compounds of Formula-I or Formula I & II; from about 6 to 14% any one or more anionic surfactants; from about 0.5 to 15% of at least one amphoteric surfactant; from about 0 to 5% of one or more non-ionic surfactant; from 0 to 4% of pearlizing or opacifying agent; from 0 to 3% of thickening agent or rheology modifier; from 0.1 to 3% of cationic conditioning agent.

In accordance with above embodiment suitable anionic surfactants include, but are not limited to alkyl sulphates, alkyl ether sulphates, alkyl sulfonates, sulfosuccinates, alkyl carboxylates, amino acid surfactants, isethionates, sulfoacetates, phosphates, and mixtures thereof, wherein the alkyl group has from about 10 to about 16 carbon atoms. Preferred anionic surfactants include sodium laureth sulphate.

As used herein, the term "amphoteric' shall mean either molecules that contain both acidic and basic sites such as, for example, an amino acid containing both amino (basic) and acid (e.g., carboxylic acid, acidic) functional groups; or Zwitterion molecules which possess both positive and negative charges within the same molecule. The charges of the latter may be either dependent on or independent of the pH of the composition. Preferably, the amphoteric surfactant is cocoamidopropyl betaine.

Therefore, the amphoteric surfactants are either electrically neutral by virtue of having balanced positive and negative charges, or they have counter ions such as alkali metal, alkaline earth, or ammonium counter ions under the pH conditions of the compositions of the present invention.

Further, the suitable non-ionic surfactants include long chain alkyl glucosides or polyglucosides with a long chain alcohol containing from about 6 to about 22, and preferably from about 8 to about 14 carbon atoms, polyoxyethylene derivatives of polyol esters like PEG-80 Sorbitan laurate and Polysorbate 20.

Commercially available pearlescent or opacifying agents which are capable of suspending water insoluble additives such as silicones and/or which tend to indicate consumers that the resultant product is a conditioning shampoo which are suitable for use in this invention. The pearlescent or opacifying agent is present in an amount, based upon the total weight of the composition, from about 0.5 percent to about 7 percent, preferably from about 3.0 percent to about 5.0 percent and more preferably, from about 1.5 percent to about 3.0 percent. Examples of suitable pearlescent or opacifying agents include, but are not limited to, mono or diesters of a) fatty acids having from about 16 to about 18 carbon atoms.

In a preferred embodiment, the pearlescent or opacifying agent is glycol esters which are introduced to the shampoo composition either as the solid form or as a preform, stabilized aqueous dispersion, commonly known as "Cold Pearlizing Concentrates" commercially available for example under the trade name Euperlan PK 3000 or Euperlan PK 4000 from BASF.

Commercially available thickening agents which are capable of imparting the appropriate viscosity to the compositions are suitable for use in this invention. Examples of suitable thickening agents nonexclusively include: fatty alkanolamides, mono or diesters of polyethylene glycol, fatty acid esters of ethoxylated polyols; ethoxylated derivatives of mono and diesters of fatty acids and glycerine; hydroxyalkyl cellulose; alkyl cellulose; hydroxyalkyl alkyl cellulose; and mixtures thereof. Preferred thickeners include alkanolamide preferably Cocamide MEA available under the trade name "Ginamide A" from the Godrej Industries Limited (Chemicals), India or polyethylene glycol ester, and more preferably PEG-150 distearate which is available from the Godrej Industries Limited (Chemicals), Mumbai (India) under the tradename, "Gincol PEGDS6"

One or more ingredients selected from a group of active ingredients consisting of conditioning agents, humectants, herbal extracts, emollients, other formulations excipients such as stabilizers, chelating agents and additives which enhance their appearance, feel such as colorants, fragrances. Preservatives, pH adjusting agents and the like, if any, can also be incorporated in the compositions of the present invention.

Examples of suitable cationic conditioning agents include cationic cellulose derivatives, cationic guar derivatives, diallyldimethylammonium chloride, and mixtures thereof. It includes Polyquaternium 7, Polyquaternium 10, Polymer JR 400 from Amerchol and Jaguar C17 from Rhodia. Commercially available secondary conditioners such as silicones, which impart, additional attributes, such as gloss to the hair are suitable to use in this invention.

Examples of Suitable chelating agents include those which are capable of protecting and preserving the compositions of this invention. Preferably, the chelating agent is disodium EDTA, and more preferably is tetrasodium EDTA and is present in an amount, based upon the total weight of the composition, from about 0 to about 0.5 percent, and preferably from about 0.05 percent to about 0.25 percent.

Personal care composition in general is moreover necessary to add preservative agents to preserve the composition from contamination by microorganisms such as bacteria, yeast & fungi, which can cause infections in man. However, the disadvantage associated with the use of preservative agents is that for them to be efficacious they must often be utilized in concentrations, which are irritating or sensitizing for the tissue with which they come in contact.

Since, the compounds of the present invention also work as a preservative, in addition to their anti-dandruff activity in the concentrations used in the personal care compositions, this obviates the need to add preservatives separately hence is more beneficial than conventional anti-dandruff compounds.

The present invention therefore has the purpose of providing a personal care composition provided with the functional properties indicated above which does not have the disadvantages associated with the conventional compounds.

The present invention also provides method of treating the disease of dandruff and symptoms associated with it comprising of the topical application of an effective amount of the personal care composition.

The pH of the compositions of this invention preferably maintained in the range of from about 4.0 to about 7.0 more preferably from about 4.5 to about 6.0 in order for the antifungal activity to be preserved at the optimum level. The compositions according to the invention are stable and homogeneous over time within a temperature range between 4 and 45° C., when tested as per standard storage stability protocols. They are well tolerated by the skin and also have good foaming and washing power, which allows the removal of dandruff and good rinsability.

Following examples of formulations will illustrate the invention.

EXAMPLES

Several examples are set forth below to further illustrate the nature of the invention and the manner of carrying it out. However, the invention should not be considered as being limited to the details thereof.

The compositions described below are expressed as weight percentages of active materials. The weight percentages of the corresponding commercial products used have been specified.

| | |
|---|---|
| Undecylenamidopropyl PG-Dimonium Chloride Phosphate | 50 ± 2% |
| Undecylenamidopropyl PG-Dimonium Chloride Phosphate + Sophorolipids | 50 ± 2% |

Process for Manufacturing of Compound of the Undecylenamidopropyl PG-Dimonium Chloride Phosphate+Sophorolipids The antidandruff composition containing combination of undecylenic acid based phosphobetaine+Sophorolipids is produced by cold mixing of Synthetic Phospholipids of Formula I and Sophorolipids of Formula II in various proportions.

Example 1

Transparent Shampoo

| Ingredients | INCI Name | % | % | Supplier |
|---|---|---|---|---|
| Aqua | Aqua | qs to 100 | qs to 100 | |
| Disodium EDTA | Di Sodium EDTA | 0.15 | 0.15 | |
| Godrej SLES L24 | Sodium laureth sulfate 28% | 42.8 | 42.8 | Godrej Industries Limited |
| Ginamide B | Cocamidopropyl betaine 30% | 6.6 | 6.6 | Godrej Industries Limited |
| Ginamide A | Cocamide MEA | 2.0 | 2.0 | Godrej Industries Limited |
| UDAP PB | Undecylenamidopropyl PG-Dimonium Chloride Phosphate | 2.0 | — | Godrej Industries Limited |
| UDAP PB + Sophorolipids | Undecylenamidopropyl PG-Dimonium Chloride Phosphate & Sophorolipid (50:50 w/w ratio) | — | 2.0 | Godrej Industries Limited |
| Preservative | Preservation | qs | qs | |
| Fragrance, dye | Fragrance, dye | qs | qs | |
| Citric acid (16% aq.) | Citric acid | qs | qs | |

Shampoo Characteristics:

Appearance: Totally transparent viscous liquid pH: 4.5-5.0, Viscosity: 5000-6000 cps Forms excellent, stable, copious foam which is easy to rinse out Stable formulation, tested at +4 C. and 45° C. (1 month)

Comparison of Anti-Dandruff Efficacy Against *M. furfur* (Zone of Inhibition)

| Sample | Active Conc. % | Zone of Inhibition (ZOI) in mm | Comments |
|---|---|---|---|
| UDAP PB | 1 | 28 | Effective |
| UDAP PB + Sophorolipid | 1 | 30 | Effective |
| ZnPTO | 1 | 34 | Effective |
| UDAP PB | 2 | 33 | Effective |
| UDAP PB + Sophorolipid (50:50 w/w) | 2 | 39 | Effective |
| ZnPTO | 2 | 41 | Effective |

From this set of results, it is concluded that the compounds of the invention are as effective as ZnPTO in anti-dandruff properties.

Time Kill Method (at 1% AI) Against Test Organism *M. furfur*.

| Sample | Exposure Time | Count of Test Organism | | | | Antimicrobial Activity | |
|---|---|---|---|---|---|---|---|
| | | Initial Count | | After Exposure | | | |
| | | CFU/ml | Log | CFU/ml | Log | Log Reduction | Percentage reduction |
| UDAP PB | 1 minute | $1.56 \times 10^5$ | 5.19 | <10 | <1 | >4.19 | >99.99 |
| | 5 minutes | | | <10 | <1 | >4.19 | >99.99 |
| UDAP PB + Sophorolipid (50:50 w/w) | 1 minute | $1.05 \times 10^5$ | 5.02 | <10 | <1 | >4.02 | >99.98 |
| | 5 minutes | | | <10 | <1 | >4.02 | >99.98 |
| UDAP CB | 1 minute | $1.54 \times 10^5$ | 5.18 | $1.37 \times 10^3$ | 3.13 | 2.05 | 99.11 |
| | 5 minutes | | | $1.10 \times 10^3$ | 3.04 | 2.14 | 99.28 |
| UDAP TMS | 1 minute | $1.58 \times 10^5$ | 5.19 | $1.10 \times 10^2$ | 2.0 | 3.19 | 99.93 |
| | 5 minutes | | | 80 | 1.9 | 3.29 | 99.94 |
| ZnPTO | 1 minute | $1.78 \times 10^5$ | 5.25 | <10 | <1 | >3.95 | >99.98 |
| | 5 minutes | | | <10 | <1 | >3.95 | >99.98 |

From this set of results, it is concluded that the compounds of the invention 1 & invention 2 shows superior anti-dandruff activity (>4 log reduction/>99.9%/reduction test bacteria *Malassezia furfur* in 1 minute and 5 minutes when analysed as per ASTM E 2315-16 methods than the prior art compounds based on undecylenic acid.

Example 2

Comparative Substantivity Properties by Rubine Dye Test

Substantivity is defined as the ability of the substance (usually cationic) to be attracted to an anionic surface such as hair and wool. Substantivity is taken as a conditioning efficacy parameter for hair and skin care products. In the industry, the Rubine Dye Uptake Test is typically performed to screen for the property of substantivity. A control fabric swatch of wool is treated in water without any treatment with a compound. The test articles, i.e., fabric swatches, are applied with a certain level of "activity" to the same weight fabric swatches as the control swatch. The treated fabric swatches are rinsed and then further treated in a solution of anionic acid dye such as Rubine Red Dye. The treatment with dye solution allows the fabric to attract the strong anionic dye solution with the help of a quaternary compound that has been applied to the swatch. The depth of colour is stronger or weaker depending upon the substantivity (higher or lower) of the quaternary. Deeper the colour, greater is the substantivity of the quaternary ammonium compound.

The Rubine Dye Uptake Test was performed using the following materials:
 1. Wool (Worsted) Swatches:
    Size=5.0×2.5 inches, Weight=1.5 µm
 2. Dye Solution: 0.50 gm Dye (Direct Red #180, Colour Index 35780 obtained from Sigma-Aldrich
    0.125 gm glacial acetic acid
    QS water 1000 ml
 3. Dye Solution for Test Swatch: 150 ml for each swatch
 4. Test sample quaternary solution: 0.5% active quaternary in water
    (2.0 gm of active quaternary in 200 ml water)
Procedure:
The control swatch is treated in water without quaternary compound. Separate swatches for each quaternary substance are treated for 5 minutes with mild stirring in separate beakers. The swatches are then individually (separately) rinsed with water. The control swatch and treated swatches are further treated (each one in a separate beaker) with dye solution for 5 minutes and rinsed in tap water at 40° C. The swatches are allowed to air dry. The depth of the dye uptake is compared. The higher the colour depth, the higher is the substantivity of the quaternary. The results of the test are shown in the following FIG. 1.

Figure 1:
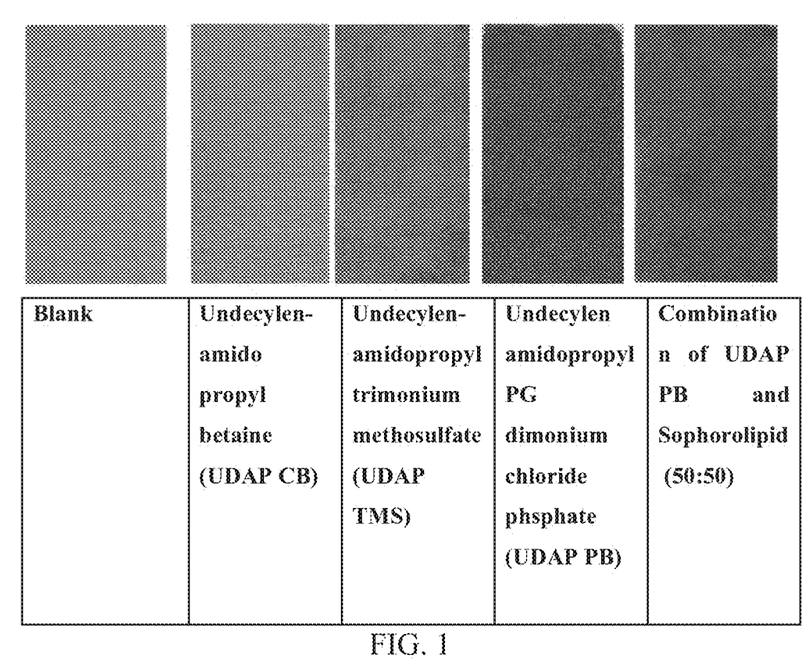
FIG. 1 illustrates the results of Rubine Dye Uptake Test for the compound and the blend for current invention.

As can be seen in FIG. 1, the products of the invention 1 and 2, shows superior substantivity as compared to other products. This is indicative of high substantivity for its use as a conditioning agent for hair care products. Hair is similar to wool fibres. Accordingly, wool is used as a sample textile material, serving a dual purpose in testing quaternaries.

Example 3

Comparative Hair Substantivity by Rubine Dye Test (at 1% AI)

The Rubine dye test is a quick and selective test that can be performed to identify cationic moiety on the hair as well as establish how long this cationic moiety will remain on the hair through washings. The anionic Rubine dye (direct red 80) complexes with cationic materials are deposited on the hair by the test product. The hair is then rinsed with tap water and visually evaluated for the presence of a pink colour. The intensity of the colour (pink to purple) is an indication of the presence and the relative amount of the quaternary compound that is bound to the hair. Throughout these test procedures, colourless Indian human hair was employed, which was purchased from International Hair exporters.

Figure 2:
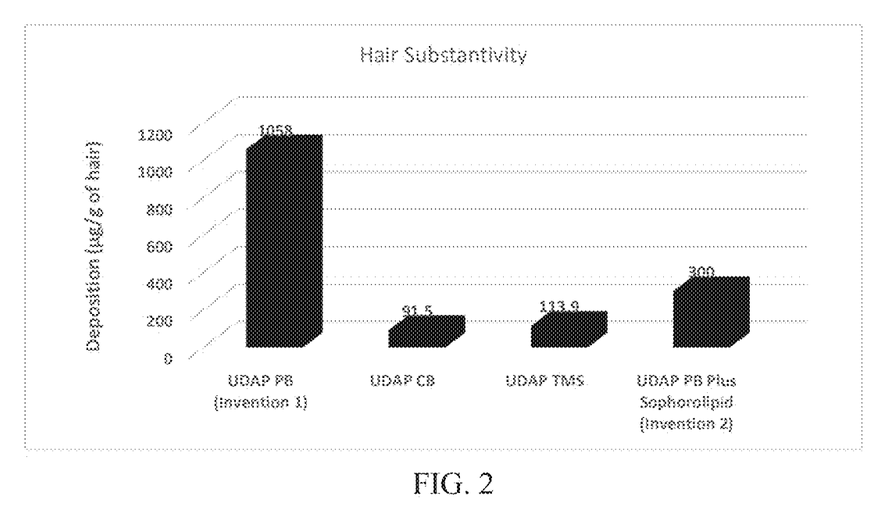
FIG. 2 illustrates a graphical comparison of the hair substantivity.

As can be seen in FIG. 2, the products of the invention 1 and 2, shows superior hair substantivity as compared to other products, indicating the use compounds of the present invention as a conditioning agent for hair care products.

Example 4

Irritancy Potential of the Compounds of the Invention by Zein Test

The Zein test enables to determine the irritation potential (harshness) of a surfactant-based product (shower gel, shampoo, soap, washing-up liquid, etc.). It consists in making soluble a yellow corn protein that is similar to the keratin present in the skin and hair. The irritation potential of the product is directly proportional to the quantity of dissolved proteins. The Zein Test provides a rapid and convenient screen for irritation potential, especially for compositions that contain surface active agents.

The Zein Test is described in detail in: E. Gotte, Skin compatibility of tensides measured by their capacity for dissolving zein protein, Proc. IV International Congress of Surface Active Substances, Brussels, 1964, pp 83-90.

This method involves measuring the solubility of zein (corn protein) in cleansing base solutions as follows.

Procedure

To 40 mL of samples, 2 f 0.05 g of zein from corn was added. The solutions with zein were shaken in a shaker with water bath (60 min. at 35° C.). The solutions were filtered on Whatman No. 1 filters and then centrifuged at 5000 rpm for 10 min. The nitrogen content in the solutions was determined by Kjeldahl method. One millilitre of the filtrate was mineralized in sulfuric acid (98%) containing copper sulphate pentahydrate and potassium sulphate. After mineralization, the solution was transferred (with 50 mL of Milli-Q water) into the flask of the Wagner-Parnas apparatus. In the next step, 20 mL of sodium hydroxide (25 wt. %) was added. The released ammonia was distilled with steam. Ammonia was bound by sulfuric acid (5 mL of 0.1 N H2SO4) in the receiver of the Wagner-Parnas apparatus. The unbound sulfuric acid was titrated with 0.1 N sodium hydroxide. Tashiro solution was used as an indicator.

The zein number (ZN) was calculated from the equation:

$$ZN=(10-V1)\cdot 100\cdot 0.7 \ [mg \ N/100 \ mL]$$

where VI is the volume (cm³) of sodium hydroxide used for titration of the sample. The final result was the arithmetic mean of five independent measurements. Sodium lauryl sulfate and cocamidopropyl betaine are taken as positive and negative control respectively.

If the value is above 400 mg N/100 mL, products are classified as strongly irritant to the skin; in the range of 200-400 mg N/100 mL, moderately irritant; and below 200 mg N/100 mL, non-irritant.

| Product | Zein Number (ZN) mg N/100 mL |
|---|---|
| Sodium lauryl sulfate | 600 |
| Cocamidopropyl betaine | 112.6 |
| UDAP PB | 36 |
| UDAP PB + Sophorolipids (50:50 w/w) | 9.35 |

It is clearly seen from the above table that, the products of the invention 1 and 2, shows very low zein number indicating that they are non-irritant to skin compared to control samples.

Example 5

Anti-dandruff Efficacy of compounds of UDAP PB+ Sophorolipids through other formulations against *M. furfur.*
Anti-Dandruff Hair Conditioner

| INCI Name | % |
|---|---|
| Demineralized water | qs to 100 |
| Di Sodium EDTA | 0.15 |
| Glycerine | 3.0 |
| Cetyl trimonium chloride 30% | 3.4 |
| Behenyl trimonium chloride 80% | 2.4 |
| Undecylenamidopropyl PG-Dimonium Chloride Phosphate & Sophorolipid) (75:25 w/w) | 3.0 |
| Preservative | Qs |
| Fragrance, dye | Qs |
| Citric acid | Qs |

Characteristics:
Appearance: Opaque Cream
pH: 4.1
Brookfield Viscosity: 30000-40000 cps Example 6

Anti-Dandruff Hair Tonic

| INCI Name | % |
|---|---|
| Demineralized water | qs to 100 |
| Di Sodium EDTA | 0.15 |
| Guargum | 0.3 |
| Bis-hydroxyethyl PG-monium chloride phosphate | 3.0 |
| Undecylenamidopropyl PG-Dimonium Chloride Phosphate | 2.0 |
| Preservative | qs |
| Fragrance, dye | qs |
| Citric acid | qs |

Characteristics:
Appearance: Clear transparent thin liquid
pH: 5.8

The anti-dandruff efficacy of hair conditioner and scalp serum/hair tonic is shown in the following table.

| Sample @ 1.5% level | Test Organism | Exposure Time | Initial Count CFU/ml | Log | After Exposure CFU/ml | Log | Antimicrobial Activity Log Reduction | Percentage reduction |
|---|---|---|---|---|---|---|---|---|
| Hair Tonic | *M. Furfur* | 1 minute | 8.05 × 10⁴ | 4.90 | <10 | <1 | >3.90 | >99.98 |
| Hair Conditioner | | 1 minute | 8.05 × 10⁴ | 4.90 | <10 | <1 | >3.90 | >99.98 |

Example 7

Antibacterial Efficacy of the Present Inventions by (MIC)

The minimum inhibitory concentration (MIC) of an antibacterial is the maximum dilution of the product that will still inhibit the growth of a test microorganism. In Tube/Plate dilution method, serial dilutions of the products are made in bacterial growth media, incubated, and scored for growth. It was determined by Tube/Plate method.

| Test Organism | UDAP PB MIC (ppm) | UDAP PB + Sophorolipids (50:50 w/w) MIC (ppm) |
|---|---|---|
| Staph. aureus | <300 | <3000 |
| Escherichia coli | <300 | <3000 |
| Ps. aeruginosa | <700 | <8000 |
| Candida albicans | <200 | <10000 |

As can be seen from the table, compounds of the invention 1 & invention 2 both are effective antibacterial against gm +ve and gm −ye micro-organism.

Example 8

Total Anti-Dandruff Lotion

| INCI Name | % |
|---|---|
| Demineralized water | qs to 100 |
| Di Sodium EDTA | 0.1 |
| Glycerine | 2.0 |
| Coconut oil | 10.0 |
| Cetearyl alcohol and Cetearyl 20 mole ethoxylate | 5.0 |
| Steareth 2 | 3.0 |
| Undecylenamidopropyl PG-Dimonium Chloride Phosphate & Sophorolipid (50:50) | 3.0 |
| Polyquaternium 7 | 0.5 |
| Preservative | qs |
| Fragrance, dye | qs |
| Citric acid | qs |

Characteristics:
Appearance: White
pH: 5.5
Brookfield Viscosity ~28000 cps

Example 9

Anti-Dandruff Gel

| Ingredients | INCI Name | % | % |
|---|---|---|---|
| Aqua | Demineralized water | qs to 100 | qs to 100 |
| Disodium EDTA | Di Sodium EDTA | 0.05 | 0.05 |
| HPMC | Hydroxypropyl methyl cellulose | 1.0 | 1.0 |
| Invention 2 (75:25 w/w) | Undecylenamidopropyl PG-Dimonium Chloride Phosphate & Sophorolipid | — | 2.0 |
| Preservative | Preservative | qs | Qs |
| Fragrance, dye | Fragrance, dye | qs | Qs |
| Citric acid (10% aq.) | Citric acid | qs | Qs |

Hair Gel Characteristics:
Appearance—Clear transparent gel
Viscosity~48500 cps
pH—6.9

We claim:

1. A water-soluble antifungal agent of Formula I,

Formula I wherein R is $CH_2=CH(CH_2)_8-$.

2. The compound as claimed in claim 1, wherein the antifungal agent of Formula I is produced by reacting a tertiary amine having an undecyl ($C_{11}$) carbon chain of Formula III:

Formula III or a tertiary amine of Formula IV having an undecylenamide moiety:

Formula IV and a phosphate ester of Formula V:

Formula V

3. A personal care cleansing composition, comprising:
from 0.5 to 4% of the antifungal agent of claim 1,
from about 6% to 14% of an anionic surfactant;
from about 0.5% to 15% of an amphoteric surfactant;
from about 0% to 5% of a non-ionic surfactant;
from 0% to 4% of a pearlizing or opacifying agent;
from 0% to 3% of a thickening agent or a rheology modifier; and
from 0.1% to 3% of a cationic conditioning agent.

4. The personal care cleansing composition as claimed in claim 3, wherein the pH of the personal care cleansing composition is in a range of 4.0 to 7.0.

5. The personal care cleansing composition as claimed in claim 3, wherein the anionic surfactant has an alkyl group having about 10 to about 16 carbon atoms, wherein the anionic surfactant is selected from the group consisting of alkyl sulphates, alkyl ether sulphates, alkyl sulfonates, sulfosuccinates, alkyl carboxylates, amino acid surfactants, isethionates, sulfoacetates, phosphates, and mixtures thereof.

6. The personal care cleansing composition as claimed in claim 3, wherein the amphoteric surfactant is an amino acid containing both an amino group and an acid functional group, or the amphoteric surfactant is a Zwitterionic surfactant.

7. The personal care cleansing composition as claimed in claim 6, wherein the amphoteric surfactant is cocoamidopropyl betaine.

8. The personal care cleansing composition as claimed in claim 3, wherein the non-ionic surfactant is selected from the group consisting of long chain alkyl glucosides with an alkyl group containing from about 6 to about 22 carbon atoms, polyglucosides with an alkyl group containing from about 6 to about 22 carbon atoms, and polyoxyethylene derivatives of polyol esters.

9. The personal care cleansing composition as claimed in claim 3, wherein the pearlizing or opacifying agent is selected from the group consisting of mono or diesters of fatty acids having from about 16 to about 18 carbon atoms.

10. The personal care cleansing composition as claimed in claim 3, further comprising a conditioning agent, a humectant, an herbal extract, an emollient, a stabilizer, a chelating agent, a colorant, a fragrance, a preservative, a pH adjusting agent, or a mixture thereof.

11. A blend of the antifungal agent of claim 1 and a compound of Formula (A), Formula II(B), or a mixture thereof:

Formula II(A)

A

Formula II(B)

B

12. The blend as claimed in claim 11, where the compound of Formula II(A), Formula II(B), or the mixture thereof is a sophorolipid produced by a yeast selected from the group consisting of *Candida bombicola, Yarrowi alipolytica, Candida apicola*, and *Candida bogoriensis*.

13. A personal care cleansing composition, comprising:

from 0.5 to 4% of the blend as claimed in claim 11, from about 6% to 14% of an anionic surfactant;

from about 0.5% to 15% of an amphoteric surfactant;

from about 0% to 5% of a non-ionic surfactant;

from 0% to 4% of a pearlizing or opacifying agent;

from 0% to 3% of a thickening agent or a rheology modifier; and from 0.1% to 3% of a cationic conditioning agent.

14. The personal care cleansing composition as claimed in claim 13, wherein the pH of the composition is in a range of 4.0 to 7.0.

15. The personal care cleansing composition as claimed in claim 13, wherein the anionic surfactant has an alkyl group having about 10 to about 16 carbon atoms, wherein the anionic surfactant is selected from the group consisting of alkyl sulphates, alkyl ether sulphates, alkyl sulfonates, sulfosuccinates, alkyl carboxylates, amino acid surfactants, isethionates, sulfoacetates, phosphates, and mixtures thereof.

16. The personal care cleansing composition as claimed in claim 13, wherein the amphoteric surfactant is an amino acid containing both an amino group and an acid functional group, or the amphoteric surfactant is a Zwitterionic surfactant.

17. The personal care cleansing composition as claimed in claim 13, wherein the non-ionic surfactant is selected from the group consisting of long chain alkyl glucosides with an alkyl group containing from about 6 to about 22 carbon atoms, polyglucosides with an alkyl group containing from about 6 to about 22 carbon atoms, and polyoxyethylene derivatives of polyol esters.

18. The personal care cleansing composition as claimed in claim 13, wherein the pearlizing or opacifying agent is selected from the group consisting of mono or diesters of fatty acids having from about 16 to about 18 carbon atoms.

19. The personal care cleansing composition as claimed in claim 3, wherein the personal care cleansing composition has broad spectrum antimicrobial activity, viscosity boosting properties, and anti-dandruff properties.

20. The personal care cleansing composition as claimed in claim 13, wherein the personal care cleansing composition has broad spectrum antimicrobial activity, viscosity boosting properties, and anti-dandruff properties.

* * * * *